United States Patent [19]

Merger et al.

[11] Patent Number: 4,999,453
[45] Date of Patent: Mar. 12, 1991

[54] PREPARATION OF OLEFINICALLY UNSATURATED CARBOXYLIC ESTERS HAVING A TERMINAL ESTER GROUP

[75] Inventors: Franz Merger, Frankenthal; Hans Horler, Darmstadt; Wolfgang Hoelderich, Frankenthal; Tom Witzel, Ludwigshafen, all of Fed. Rep. of Germany

[73] Assignee: BASF Aktiengesellschaft, Ludwigshafen, Fed. Rep. of Germany

[21] Appl. No.: 337,867

[22] Filed: Apr. 14, 1989

[30] Foreign Application Priority Data

Apr. 20, 1988 [DE] Fed. Rep. of Germany ....... 3813147

[51] Int. Cl.$^5$ .............................................. C07C 67/30
[52] U.S. Cl. .................................... 560/211; 560/104; 560/128
[58] Field of Search .................... 560/211, 104, 128; 585/640

[56] References Cited

U.S. PATENT DOCUMENTS

| | | | |
|---|---|---|---|
| 3,530,198 | 9/1970 | Fenton | 260/682 |
| 3,625,996 | 12/1971 | Fenton | 560/211 |
| 4,102,938 | 7/1978 | Rao | 260/676 R |
| 4,178,317 | 12/1978 | Horn et al. | 585/357 |
| 4,471,148 | 9/1984 | Vogt | 585/640 |

FOREIGN PATENT DOCUMENTS 0135436 8/1986 European Pat. Off. .
2726106 12/1978 Fed. Rep. of Germany .

Primary Examiner—Paul J. Killos
Attorney, Agent, or Firm—Keil & Weinkauf

[57] ABSTRACT

Olefinically unsaturated carboxylic esters having a terminal ester group and of the general formulae Ia and Ib $$R^1-CH_2-CH=CH-(CH_2)_{r-1}-COOR^2 \qquad (Ia)$$

$$R^1-CH=CH-(CH_2)_r-COOR^2 \qquad (Ib)$$

and, if desired, further double bond isomers, where $R^1$ is hydrogen or an organic radical, $R^2$ is $C_1$-$C_8$-alkyl and r is from 1 to 20, are prepared by a process in which an α-substituted α,ω-(n-alkylenedicarboxylic ester) of the general formula II

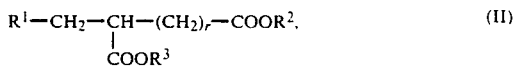

where $R^1$ and $R^2$ and r have the abovementioned meanings and $R^3$ is $C_1$-$C_8$-alkyl, is converted over an acidic heterogeneous catalyst at from 150° to 800° C. and under from 0.01 to 50 bar.

8 Claims, No Drawings

PREPARATION OF OLEFINICALLY UNSATURATED CARBOXYLIC ESTERS HAVING A TERMINAL ESTER GROUP

The present invention relates to a process for the preparation of olefinically unsaturated carboxylic esters having a terminal ester group by retrocarbonylation of α-substituted α,ω-(n-alkylenedicarboxylic esters).

EP-A-135 436 discloses that carboxylic acids and their esters having a terminal ester group are converted, over a catalyst which contains nickel as well as one or more of the metals tin, germanium and lead, at from 200° to 400° C., into alkenes whose carbon skeleton is shorter than that of the starting materials by one carbon atom.

According to U.S. Pat No. 4,102,938, thermolysis of vegetable oils (glycerides of n-carboxylic acids) in the presence of transition metal-doped silicon/alumina catalysts at from 300° to 700° C. gives hydrocarbon mixtures which, in addition to olefins, contain saturated hydrocarbons and also crack products.

Japanese Preliminary Published application No. 47904/1975 (application No. 95 944/1973) discloses the retrocarbonylation of aliphatic and alicyclic carboxylic esters with phosphorus tungsten oxides on silica. Propylene and carbon monoxide and the alkene corresponding to the bonded alcohol are thus formed from isobutyrates in the gas phase at about 250° C.

According to DE-A-27 26 106, monocarboxylic acids having a terminal or α-substituted carboxyl group or their esters can be decarboxylated under dehydrogenating conditions in the gas phase at from 250° to 800° C. over aluminum/boron oxide catalysts with the formation of unsaturated hydrocarbons, and partial rearrangements of the skeletons have been observed.

U.S. Pat No. 3,530,198 discloses that, with the aid of a catalyst complex consisting of a noble metal and, for example, diphenylphosphine, a mixture of a carboxylic ester having a terminal ester group and an α-substituted carboxylic ester can be converted into the olefin with retrocarbonylation, no difference being observed.

It is an object of the present invention selectively to remove from dicarboxylic esters the carboxylic ester group on the more highly substituted carbon atom.

We have found that this object is achieved by a process for the preparation of olefinically unsaturated carboxylic esters having a terminal ester group and of the general formulae Ia and Ib $$R^1-CH_2-CH=CH-(CH_2)_{r-1}-COOR^2 \quad (Ia)$$

$$R^1-CH=CH-(CH_2)_r-COOR^2 \quad (Ib)$$

and, if desired, further double bond isomers, where $R^1$ is hydrogen or an organic radical, $R^2$ is $C_1-C_8$-alkyl and r is from 1 to 20, by retrocarbonylation, wherein an α-substituted α,ω-(n-alkylenedicarboxylic ester) of the general formula II

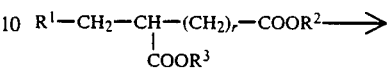

where $R^1$ and $R^2$ and r have the abovementioned meanings and $R^3$ is $C_1-C_8$-alkyl, is converted over an acidic heterogeneous catalyst at from 150° to 800° C. and under from 0.01 to 50 bar.

The olefinically unsaturated carboxylic esters having a terminal ester group are obtainable by the following method:

The reaction takes place according to the following equation when an α-substituted α,ω-(n-alkylenedicarboxylic ester) II is brought into contact with a catalyst:

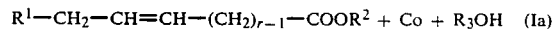

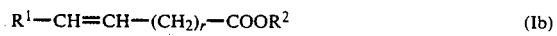

The alkenecarboxylic esters Ia and Ib can form further double bond isomers under the reaction conditions if $R^1$ and r permit this.

The reaction can be carried out batchwise or, preferably, continuously, preferably in the gas phase at from 150° to 800° C. and under from 0.01 to 50 bar.

However, it is also possible to carry out a liquid-phase reaction at from 50° to 200° C. and under from 0.5 to 5 bar.

The preferred gas-phase reaction can be carried out, for example, at from 150° to 800° C., preferably from 200° to 600° C., and under from 0.1 to 5 bar, particularly preferably at from 280° to 500° C. and under from 0.5 to 2 bar. In the reaction in the gas phase, it is advantageous to maintain a space velocity (WHSV) of from 0.01 to 40, in particular from 0.05 to 10, g of starting material of the formula II per g of catalyst per hour. The gas phase reaction can be carried out in a fixed bed or fluidized bed.

After the reaction, the resulting products are isolated from the reaction mixture by a conventional method, for example by distillation; unconverted starting materials are, if required, recycled to the reaction.

$R^1$ in formulae Ia, Ib and II may be hydrogen or alkyl, for example of 1 to 10, in particular 1 to 8, carbon atoms, such as methyl, ethyl, propyl, isopropyl, butyl, isobutyl, tert-butyl, pentyl, isopentyl, hexyl, heptyl or octyl; cycloalkyl, for example of 4 to 8, in particular 5 or 6, carbon atoms, such as cyclopentyl or cyclohexyl; or aryl or aralkyl. Aryl radicals are, for example, phenyl or phenyl radicals which carry inert substituents, for example $C_1-C_4$-alkyl-, $C_1-C_4$-alkoxy- or halogen-substituted phenyl. Aralkyl radicals are, for example, benzyl, and the phenyl nucleus may carry the abovementioned substituents. Hydrogen and methyl are particularly preferred.

In formulae Ia, Ib and II, $R^2$ and $R^3$ independently of one another are each alkyl of 1 to 8, preferably 1 to 4, carbon atoms, such as methyl, ethyl, propyl, isopropyl, butyl, isobutyl or, particularly preferably, methyl.

The index r in formulae Ia, Ib and II is from 1 to 20, preferably from 1 to 8, particularly preferably from 1 to 4.

Examples of starting materials of the formula II and, in parentheses, the corresponding end products are:

| | |
|---|---|
| Dimethyl methylsuccinate | (→ methyl n-butenoate) |
| Dimethyl ethylsuccinate | (→ methyl n-pentenoate) |

-continued

| | |
|---|---|
| Dimethyl n-propylsuccinate | (→ methyl n-hexenoate) |
| Dimethyl n-butylsuccinate | (→ methyl n-heptenoate) |
| Dimethyl n-pentylsuccinate | (→ methyl n-octenoate) |
| Dimethyl 2-methylglutarate | (→ methyl n-pentenoate) |
| Dimethyl 2-ethylglutarate | (→ methyl n-hexenoate) |
| Dimethyl 2-(n-propyl)-glutarate | (→ methyl n-heptenoate) |
| Dimethyl 2-(n-butyl)-glutarate | (→ methyl n-octenoate) |
| Dimethyl 2-methyladipate | (→ methyl n-hexenoate) |
| Dimethyl 2-ethyladipate | (→ methyl n-heptenoate) |
| Dimethyl 2-(n-propyl)-adipate | (→ methyl n-octenoate) |
| Dimethyl 2-methylpivalate | (→ methyl n-heptenoate) |
| Dimethyl 2-ethylpivalate | (→ methyl n-octenoate) |
| Diethyl methylsuccinate | (→ ethyl n-butenoate) |
| Diethyl ethylsuccinate | (→ ethyl n-pentenoate) |
| Diethyl n-propylsuccinate | (→ ethyl n-hexenoate) |
| Diethyl n-butylsuccinate | (→ ethyl n-heptenoate) |
| Diethyl n-pentylsuccinate | (→ ethyl n-octenoate) |
| Diethyl 2-methylglutarate | (→ ethyl n-pentenoate) |
| Diethyl 2-ethylglutarate | (→ ethyl n-hexenoate) |
| Diethyl 2-(n-propyl)-glutarate | (→ ethyl n-heptenoate) |
| Diethyl 2-(n-pentyl)-glutarate | (→ ethyl n-octenoate) |
| Diethyl 2-methyladipate | (→ ethyl n-hexenoate) |
| Diethyl 2-ethyladipate | (→ ethyl n-heptenoate) |
| Diethyl 2-(n-propyl)-adipate | (→ ethyl n-octenoate) |
| Diethyl 2-methylpivalate | (→ ethyl n-heptenoate) |
| Diethyl 2-ethylpivalate | (→ ethyl n-octenoate) |

The acidic heterogeneous catalysts used are, in particular, acidic zeolites, phosphates or acidic oxides of elements of main groups three and four and of subgroups two to six of the Periodic Table.

Zeolite catalysts are particularly advantageously used.

Zeolites are crystalline aluminosilicates which have a highly ordered structure with a rigid three-dimensional network of $SiO_4$ and $AlO_4$ tetrahedra which are bonded by common oxygen atoms. The ratio of Si and Al atoms to oxygen is 1:2. The electrovalency of the aluminum-containing tetrahedra is balanced by the inclusion of cations in the crystal, for example an alkali metal ion or hydrogen ion; cation exchange is possible.

Catalysts which are suitable for the novel process are zeolites of the mordenite group or narrow-pore zeolites of the erionite or chabasite type or zeolites of the faujasite type, for example Y, X or L zeolites. This group of zeolites includes the ultrastable zeolites of the faujasite type, i.e. dealuminated zeolites.

Zeolites having the pentasil structure are particularly advantageous. These possess, as a common basic building block, a 5-membered ring composed of $SiO_4$ tetrahedra. They have a high $SiO_2/Al_2O_3$ ratio and pore sizes which are between those of the zeolites of type A and those of type X or Y.

These zeolites may have different chemical compositions. They are aluminosilicate, borosilicate, iron silicate, beryllium silicate, gallium silicate, chromium silicate, arsenic silicate, antimony silicate and bismuth silicate zeolites or mixtures of these, as well as aluminogermanate, borogermanate, gallium germanate and iron germanate zeolites or mixtures of these. The aluminosilicate, borosilicate and iron silicate zeolites having the pentasil structure are particularly suitable for the novel process.

The aluminosilicate zeolites are prepared, for example, from an aluminum compound, preferably $Al(OH)_3$ or $Al_2(SO_4)_3$, and a silicon component, preferably finely divided silica, in aqueous amine solution, in particular in polyamines, such as 1,6-hexanediamine or 1,3-propanediamine or triethylenetetramine solution, with or, in particular, without the addition of an alkali metal compound or alkaline earth metal compound, at from 100 to 220° C. under autogenous pressure. These also include the isotactic zeolites. The aluminosilicate zeolites obtained have an $SiO_2/Al_2O_3$ ratio of from 10 to 40,000, depending on the choice of the amounts of starting materials. Aluminosilicate zeolites of this type can also be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali metal compound or alkaline earth metal compound. These also include the isotactic zeolites. Such borosilicate zeolites can likewise be prepared if the reaction is carried out in ether solution, eg. diethylene glycol dimethyl ether, or in alcoholic solution, eg. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali metal compound or alkaline earth metal compound, at from 100° to 220° C. under autogenous pressure.

The silicon-rich zeolites ($SiO_2/Al_2O_3$) which may be used include the ZSM types, ferrierite, Nu-1 and Silicalite (a molecular sieve, i.e. a silica polymorph).

The aluminosilicate, borosilicate and iron silicate zeolites thus prepared can be isolated, dried at from 100° to 160° C., preferably from 105° to 115° C., and calcined at from 450° to 550° C., preferably 500° C., and then molded with a binder in a weight ratio of from 90 : 10 to 40 : 60 to give extrudates or pellets. Suitable binders are various aluminas, preferably boehmite, amorphous aluminosilicates having an $SiO_2/Al_2O_3$ ratio of from 25 : 75 to 90 : 5, preferably 75 : 25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and is not subjected to calcination until after the molding procedure. The aluminosilicate and borosilicate zeolites prepared can be used in pure form, without a binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example, in the Na form, the latter can be converted completely or partially into the desired H form by ion exchange, for example by ammonium ions, and subsequent calcination, or by treatment with acids.

If, when the zeolite catalysts are used according to the invention, any deactivation occurs as a result of coking, it is advisable to regenerate the zeolites by burning off the coke deposit with air or with an air/$N_2$ mixture at from 400° to 550° C., preferably 500° C. As a result, the zeolites regain their initial activity.

By precoking, it is possible to adjust the activity of the catalyst to achieve optimum selectivity with respect to the desired reaction product.

In order to achieve a very high selectivity, a high conversion and long catalyst lives, it may be advantageous to modify the zeolites. In a suitable method of modifying the catalysts, for example, the unmolded or molded zeolites are doped with metal salts by ion exchange or by impregnation. The metals used are alkali metals, such as Li, Cs or K, alkaline earth metals, such as Mg, Ca or Sr, metals of subgroups 3, 4 and 5, such as Al, Ga, Ge, Sn, Pb or Bi, transition metals of subgroups 4 to 8, such as Ti, Zr, V, Nb, Cr, Mo, W, Mn, Re, Fe, Ru, Os, Co, Rh, Sr, Ni, Pd or Pt, transition metals of subgroups 1 and 2, such as Cu, Ag or Zn, or rare earth metals, such as La, Ce, Pr, Nd, Fr, Yb or U. The content of these metals is advantageously from 0.1 to 2.0% by weight.

Doping is advantageously carried out, for example, by initially taking the molded zeolite in a riser tube and passing over, for example, an aqueous or ammoniacal solution of a halide or of a nitrate of the metals described above, at from 20° to 100° C. Ion exchange of this type can be carried out, for example on the hydrogen, ammonium or alkali metal form of the zeolite. In another possible method of applying metals to the zeolite, the zeolite material is impregnated, for example with a halide, a nitrate or an oxide of the metals described above in aqueous, alcoholic or ammoniacal solution. Both ion exchange and impregnation are followed by one or more drying steps, and, if desired, repeated calcination.

In a possible embodiment, for example, $Cu(NO_3)_2 \cdot 3H_2O$ or $Ni(NO_3)_2 \cdot 6H_2O$ or $Ce(NO_3)_3 \cdot 6H_2O$ or $La(NO_3)_2 \cdot 6H_2O$ or $Cs_2CO_3$ is dissolved in water. This solution is used to impregnate the molded or unmolded zeolite for a certain time, i.e. about 30 minutes. Any supernatant solution is freed from water in a rotary evaporator. Thereafter, the impregnated zeolite is dried at about 150° C. and calcined at about 550° C. This impregnation process can be repeated several times in succession in order to obtain the desired metal content.

It is also possible to prepare, for example, an aqueous $Ni(CO_3)_2$ solution or ammoniacal $Pd(NO_3)_2$ solution and to suspend therein the pure zeolite powder at from 40° to 100° C. for about 24 hours, while stirring. After the product has been filtered off, dried at about 150° C. and calcined at about 500° C., the zeolite material obtained in this manner can be further processed with or without a binder to give extrudates, pellets or fluidizable material.

The zeolite in the H form, ammonium form or alkali metal form can be subjected to ion exchange by a procedure in which the zeolite in the form of extrudates or pellets is initially taken in a column and, for example, an aqueous $Ni(NO_3)_2$ solution or ammoniacal $Pd(NO_3)_2$ solution is circulated over the said zeolite at slightly elevated temperatures of from 30° to 80° C. for from 15 to 20 hours. Thereafter, the product is washed thoroughly with water, dried at about 150° C. and calcined at about 550° C. In the case of some metal-doped zeolites, for example Pd-, Cu- and Ni-doped zeolites, aftertreatment with hydrogen is advantageous.

In another possible method of modification, the molded or unmolded zeolite material is subjected to a treatment with acids, such as hydrochloric acid, hydrofluoric acid and phosphoric acid, and/or steam. In an advantageous procedure of this type, for example, the zeolite in powder form is treated with 1 N phosphoric acid for 1 hour at 80° C. After the treatment, the product is washed with water, dried at 110° C. for 16 hours and calcined at 500° C. for 20 hours. In another procedure, zeolites, before or after they have been molded with a binder, are treated with a 3–25, in particular 12–20, % strength by weight hydrochloric acid, for example for from 1 to 3 hours at from 60° to 80° C. The zeolite treated in this manner was then washed with water, dried, and calcined at from 400° to 500° C.

In a particular embodiment of the acid treatment, the zeolite material, before it has been molded, is treated at elevated temperatures with hydrofluoric acid, which is generally used in the form of from 0.001 to 2 N, preferably from 0.05 to 0.5 N, hydrofluoric acid, for example by refluxing for, in general, from 0.5 to 5, preferably from 1 to 3, hours. The zeolite material is isolated, for example by filtering it off and washing it thoroughly, and is then advantageously dried at, for example, from 100° to 160° C. and calcined at, in general, from 450° to 600° C. In another preferred embodiment of the acid treatment, the zeolite material is molded with a binder and then treated, preferably with from 12 to 20% strength by weight hydrochloric acid, at elevated temperatures, advantageously at from 50° to 90° C., preferably from 60° to 80° C., for from 0.5 to 5 hours. The zeolite material is then generally washed thoroughly and advantageously dried, for example at from 100° to 160° C., and calcined at, in general, from 450° to 600° C. An HF treatment may also be followed by an HCl treatment.

In another procedure, zeolites can be modified by applying phosphorus compounds, such as trimethyl phosphate, trimethoxyphosphine or primary, secondary or tertiary sodium phosphate. The treatment with primary sodium phosphate has proven particularly advantageous. Here, the zeolites, in the form of extrudates, pellets or fluidizable material, are impregnated with aqueous $NaH_2PO_4$ solution, dried at 110° C. and calcined at 500° C.

Other suitable acidic heterogeneous catalysts are sheet silicates, such as montmorillonite and bentonite.

Other catalysts for the novel process are phosphates, in particular aluminum phosphates, silicon aluminum phosphates, silicon iron aluminum phosphates, cerium phosphates, zirconium phosphates, boron phosphates, iron phosphates and mixtures of these.

In particular, aluminum phosphates synthesized under hydrothermal conditions are used as aluminum phosphate catalysts for the novel process.

The aluminum phosphates (APO) prepared under hydrothermal conditions are, for example, APO-5, APO-9, APO-11, APO-12, APO-14, APO-21, APO-25, APO-31 and APO-33. Syntheses of these compounds are described in EP-A-132 708, U.S. Pat. No. 4,310,440 and U.S. Pat. No. 4,473,663.

For example, $AlPO_4$-5 (APO-5) is synthesized by mixing orthophosphoric acid with pseudoboehmite (Catapal SB®) in water to give a homogeneous mixture. Tetrapropylammonium hydroxide is added to this mixture, which is then subjected to a reaction in an autoclave at about 150° C. for from 20 to 60 hours under autogenous pressure. The $AlPO_4$ filtered off is dried at from 100° to 160° C. and calcined at from 450° to 550° C.

$AlPO_4$-9 (APO-9) is likewise synthesized from orthophosphoric acid and pseudoboehmite, but in aqueous 1,4-diazabicyclo[2.2.2]octane solution at about 200° C.

under autogenous pressure in the course of from 200 to 400 hours.

AlPO$_4$-21 (APO-21) is synthesized from orthophosphoric acid and pseudoboehmite in aqueous pyrrolidone solution at from 150° to 200° C. under autogenous pressure in the course of from 50 to 200 hours.

The silicon aluminum phosphates (SAPO) which may be used for the novel process are, for example, SAPO-5, SAPO-11, SAPO-31 and SAPO-34. The synthesis of these compounds is described in, for example, EP-A-103 117 or U.S. Pat. No. 4,440,871. Silicon aluminum phosphates are prepared by crystallization from an aqueous mixture at from 100° to 250° C. and under autogenous pressure in the course of from 2 hours to 2 weeks, the reaction mixture consisting of a silicon component, an aluminum component and a phosphorus component being reacted in an aqueous solution containing an organic amine.

SAPO-5, for example, is obtained by mixing SiO$_2$, suspended in aqueous tetrapropylammonium hydroxide solution, with an aqueous suspension of pseudoboehmite and orthophosphoric acid and then carrying out the reaction at from 150° to 200° C. in the course of from 20 to 200 hours under autogenous pressure in a stirred autoclave. The powder filtered off is dried at from 110° to 160° C. and calcined at from 450° to 550° C.

Boron phosphates for the novel process can be prepared, for example, by mixing and kneading concentrated boric acid and by subsequent drying and calcination in an inert gas, air or steam atmosphere at from 250° to 650° C., preferably from 300° to 500° C.

Precipitated aluminum phosphates can also be used as phosphate catalysts in the process. For example, an aluminum phosphate of this type is prepared by dissolving 92 g of diammonium hydrogen phosphate in 700 ml of water. 260 g of Al(NO$_3$)$_3$.H$_2$O in 700 ml of water are added dropwise to this solution in the course of 2 hours. During this procedure, the pH is kept at 8 by the simultaneous addition of 25% strength NH$_3$ solution. The resulting precipitate is stirred for a further 12 hours and then filtered off under suction and washed thoroughly. It is dried at 60° C. for 16 hours.

A cerium phosphate used for the novel process is obtained, for example, by precipitation from 52 g of Ce(NO$_3$)$_3$.6H$_2$O and 56 g of NaH$_2$PO$_4$.2H$_2$O. After the filtration, the material is extruded and the extrudates are dried at 120° C. and calcined at 450° C.

Modifying components as described above in the case of the zeolites can be applied to these phosphates by impregnation (immersion and spraying on) or in some cases also by ion exchange. As in the case of the zeolite catalysts, modification may also be effected with an acid, for example phosphoric acid.

A catalyst containing phosphoric acid can be obtained, for example, by spraying H$_3$PO$_4$ or NaH$_2$PO$_4$ or Na$_2$HPO$_4$ solution onto a carrier, such as SiO$_2$, and then drying or calcining the product. However, it is also possible for phosphoric acid, together with silica gel, to be sprayed using a spray tower, this step being followed by drying and in general calcination. Phosphoric acid can also be sprayed onto the carrier in an impregnating mill.

Acidic oxides, for example those of elements of main groups three and four and of subgroups two to six of the Periodic Table, in particular oxides such as silica in the form of silica gel, kieselguhr or quartz, as well as zinc oxide, titanium dioxide, zirconium dioxide, phosphorus oxides, vanadium oxides, niobium oxides, boron oxides, aluminas, chromium oxides, molybdenum oxides, tungsten oxides or pumice or mixtures of these oxides may also advantageously be used for the novel process. Mixtures of the abovementioned oxides comprise, for example, alumina, such as $\gamma$-Al$_2$O$_3$, with boron oxide, silica, tungsten oxide or chromium oxide. The oxides can be doped by applying modifying components, as described above in the case of the zeolite catalysts. The treatment with acids as described for the zeolite catalysts is also a possible method of modification.

The catalysts described here can be used alternatively in the form of 2-4 mm extrudates, tablets having a diameter of from 3 to 5 mm or chips having particle sizes of from 0.05, in particular from 0.1, to 0.5 mm, or as fluidized catalysts. The fluidizable material can be prepared, for example, by comminuting and screening extrudates or by spray drying.

EXAMPLES

Example 1

Preparation of methyl 2-, 3- and 4-pentenoate from dimethyl 2-methylglutarate/dimethyl ethylsuccinate 50 g/hour of a mixture of 81% by weight of dimethyl 2-methylglutarate and 19% by weight of dimethyl ethylsuccinate, together with 100 l/hour of nitrogen, are passed from an evaporator under atmospheric pressure into a reactor (quartz tube of 20 mm internal diameter) which is heated at 500° C. and contains 50 ml of a catalyst which consists of 50% by weight of $\gamma$-Al$_2$O$_3$ and 50% by weight of B$_2$O$_3$, is in the form of 2 mm extrudates and has a bulk density of 0.50 kg/l. The reaction vapors formed are condensed. After operation for 4 hours, 184 g of reaction mixture having the following composition (quantitative GC analysis) are obtained:

74.1% by weight of dimethyl 2-methylglutarate,
19.9% by weight of dimethyl ethylsuccinate,
0.8% by weight of methyl 4-pentenoate,
1.7% by weight of methyl 3-pentenoate,
0.4% by weight of methyl 2-pentenoate and
3.1% by weight of other products which, however, do not contain any monocarboxylic esters branched in the $\alpha$-position.

Example 2

Preparation of methyl 2-, 3- and 4-pentenoate from dimethyl 2-methylglutarate/dimethyl ethylsuccinate in the presence of a borosilicate zeolite Preparation of the catalyst:

The borosilicate zeolite of the pentasil type was prepared in a hydrothermal synthesis from 640 g of finely divided SiO$_2$, 122 g of H$_3$BO$_3$ and 8,000 g of a 50% strength aqueous 1,6-hexanediamine solution at 170° C. under autogenous pressure in a stirred autoclave. The crystalline reaction product was filtered off, washed thoroughly and then dried for 24 hours at 100° C. and calcined for 24 hours at 500° C. This borosilicate zeolite contained 94.2% by weight of SiO$_2$ and 2.3% by weight of B$_2$O$_3$.

This material was molded with a molding assistant to give 2 mm extrudates, which were dried at 110° C. for 16 hours and calcined at 500° C. for 24 hours.

Reaction:

50 g/hour of a mixture of 78% by weight of dimethyl 2-methylsuccinate and 22% by weight of dimethyl ethylsuccinate were vaporized under atmospheric pressure and passed at 350° C. over the borosilicate zeolite (bulk density 0.50 kg per liter of catalyst; internal reactor diameter 20 mm). At a space velocity of 1 kg of ester mixture per liter of catalyst per hour and an inert gas throughput of 1,000 l of nitrogen per liter of catalyst per hour, 196 g of a product mixture having the following composition (quantitative GC analysis) were obtained by condensation after 4 hours:
74.7% by weight of dimethyl 2-methylglutarate,
21.2% by weight of dimethyl ethylsuccinate,
1.2% by weight of methyl 4-pentenoate,
1.9% by weight of methyl 3-pentenoate,
0.2% by weight of methyl 2-pentenoate and
0.8% by weight of other products which, however, do not contain any monocarboxylic esters branched in the α-position.

This corresponds to a total methyl pentenoate selectivity of 82% at a dimethyl 2-methylglutarate/dimethyl ethylsuccinate conversion of 6%.

Example 3

Preparation of methyl 2-, 3- and 4-pentenoate from dimethyl 2-methylglutarate/dimethyl ethylsuccinate in the presence of a borosilicate zeolite 50 g/hour of a mixture of 78% by weight of dimethyl 2-methylglutarate and 22% by weight of dimethyl ethylsuccinate were evaporated under atmospheric pressure in a quartz tube, and the educt vapors were passed, together with 50 liters of nitrogen, at 400° C., over 50 ml of the borosilicate zeolite prepared similarly to Example 2 (bulk density 0.50 g/l; internal reactor diameter 20 mm); the reaction vapors were condensed. After 4 hours, 186 g of reaction mixture having the following composition were obtained:
60.7% by weight of dimethyl 2-methylglutarate,
21.0% by weight of dimethyl ethylsuccinate,
3.6% by weight of methyl 4-pentenoate,
6.2% by weight of methyl 3-pentenoate,
2.6% by weight of methyl 2-pentenoate and
6.1% by weight of other products which, however, do not contain any monocarboxylic esters branched in the α-position.

This corresponds to a total methyl pentenoate selectivity of 73% at a dimethyl 2-methylglutarate/dimethyl ethylsuccinate conversion of 24%.

Example 4

Preparation of methyl 2-, 3- and 4-pentenoate from dimethyl 2-methylglutarate/dimethyl ethylsuccinate in the presence of a cesium-containing borosilicate zeolite Preparation of the catalyst:
Extrudates of the borosilicate zeolite (prepared similarly to Example 2) were impregnated with an aqueous CsCO3 solution and then dried at 130° C. and calcined at 540° C. for 2 hours. The Cs content was 0.6% by weight.
Reaction:
A mixture of 81% by weight of dimethyl 2-methylglutarate and 19% by weight of dimethyl ethylsuccinate was vaporized at 300° C. under atmospheric pressure and passed, at 300° C., over 50 ml of the cesium-doped borosilicate zeolite (bulk density 0.52 kg/l, internal reactor diameter 20 mm). At a space velocity of 1 kg of ester mixture per liter of catalyst per hour, 190 g of a product mixture having the following composition according to quantitative GC analysis were obtained by condensation after 4 hours:
74.1% by weight of dimethyl 2-methylglutarate,
17.4% by weight of dimethyl ethylsuccinate,
2.0% by weight of methyl 4-pentenoate,
4.1% by weight of methyl 3-pentenoate,
2.0% by weight of methyl 2-pentenoate and
0.4% by weight of other products which, however, did not contain any monocarboxylic esters branched in the α-position.

This corresponds to a total methyl pentenoate selectivity of 89% at a dimethyl 2-methylglutarate/dimethyl ethylsuccinate conversion of 13%.

Example 5

Preparation of methyl 2-, 3- and 4-pentenoate from dimethyl 2-methylglutarate/dimethyl ethylsuccinate in the presence of an aluminosilicate zeolite Preparation of the catalyst:
The aluminosilicate zeolite having a pentasil structure was prepared under hydrothermal conditions, under autogenous pressure and at 150° C., from 65 g of finely divided SiO2 and 20.3 g of Al2(SO4)3.18H2O in 1 kg of 50% strength aqueous 1,6-hexanediamine solution in a stirred autoclave. The crystalline reaction product was filtered off and washed thoroughly and then dried for 24 hours at 110° C. and calcined for 24 hours at 500° C. This aluminosilicate zeolite contained 91.6% by weight of SiO2 and 4.6% by weight of Al2O3. The catalyst was molded with a molding assistant to give 2 mm extrudates which were then dried for 16 hours at 110° C. and calcined for 24 hours at 500° C.

Reaction:
50 g/hour of an ester mixture of 78% by weight of dimethyl 2-methylglutarate and 22% by weight of dimethyl 2-ethylsuccinate were vaporized at 300° C., the gaseous ester mixture was passed, together with 50 liters of nitrogen, at 300° C., over 50 ml of the aluminosilicate zeolite (bulk density 0.50 kg/l, internal reactor diameter 20 mm) and the reaction vapors were condensed. After a reaction time of 4 hours, 196 g of a reaction mixture having the following composition were obtained:
62.9% by weight of dimethyl 2-methylglutarate,
20.8% by weight of dimethyl ethylsuccinate,
1.3% by weight of methyl 4-pentenoate,
5.7% by weight of methyl 3-pentenoate,
1.8% by weight of methyl 2-pentenoate and
7.5% by weight of other products which, however, do not contain any monocarboxylic esters branched in the α-position.

This corresponds to a dimethyl 2-methylglutarate/dimethyl ethylsuccinate conversion of 18% and a total methyl pentenoate selectivity of 73%.

We claim:
1. A process for the preparation of olefinically unsaturated carboxylic esters having a terminal ester group and of the formulae Ia and Ib

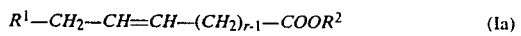

$$R^1-CH_2-CH=CH-(CH_2)_{r-1}-COOR^2 \quad (Ia)$$

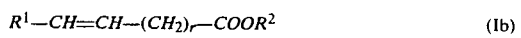

$$R^1-CH=CH-(CH_2)_r-COOR^2 \quad (Ib)$$

where $R^1$ is hydrogen, alkyl, cycloalkyl, aryl, or aralkyl, $R^2$ is C-C8-alkyl and r is from 1 to 20, which process comprises converting an α-substituted α,ω-(n-alkylenedicarboxylic ester) of the formula II

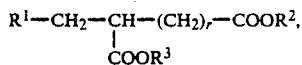

where $R^1$ and $R_2$ have the abovementioned meanings and $R^3$ is $C_1$–$C_8$-alkyl, over an acidic heterogenous catalyst at from 150° to 800° C. and under from 0.01 to 50 bar.

2. A process as claimed in claim 1, wherein the acidic heterogeneous catalysts used are oxides of main groups three or four, subgroups two to six of the Periodic Table, zeolites or phosphates.

3. A process as claimed in claim 1, wherein the catalyst used is a pentasil zeolite.

4. A process as claimed in claim 1, wherein the catalysts used are aluminum silicate, iron silicate, boron silicate or mixtures thereof.

5. A process as claimed in claim 1, wherein the catalyst used is a zeolite which has been doped with alkali metals transition metals, rare earth metals or mixtures thereof or treated with an inorganic acid.

6. A process as claimed in claim 1, wherein the acidic heterogeneous catalyst used is an aluminum phosphate, a silicon aluminum phosphate or a boron phosphate.

7. A process as claimed in claim 1, wherein the acidic heterogenous catalysts used are alumina, silica, boron oxide or mixtures thereof.

8. A process as claimed in claim 1, wherein the reaction is carried out in the gas phase at from 150° to 800° C.

* * * * *